United States Patent [19]

Beestman

[11] Patent Number: 4,534,783
[45] Date of Patent: Aug. 13, 1985

[54] HIGH CONCENTRATION ENCAPSULATION OF WATER SOLUBLE-MATERIALS

[75] Inventor: George B. Beestman, St. Louis County, Mo.

[73] Assignee: Monsanto Co., St. Louis, Mo.

[21] Appl. No.: 567,585

[22] Filed: Jan. 3, 1984

[51] Int. Cl.$^3$ ............................................. B01J 13/02
[52] U.S. Cl. ..................................... 71/27; 71/64.11; 264/4; 264/4.1; 264/4.7
[58] Field of Search ...................... 71/64.11, 27; 264/4, 264/4.1, 4.7

[56] References Cited

U.S. PATENT DOCUMENTS

| | | | |
|---|---|---|---|
| 3,429,827 | 2/1969 | Ruus | 424/19 |
| 3,575,882 | 4/1971 | Vandegaer et al. | 264/4 |
| 3,577,515 | 5/1971 | Vandegaer | 424/32 |
| 3,872,023 | 3/1975 | Baum et al. | 264/4 |
| 4,016,099 | 4/1977 | Wellman et al. | 264/4 |
| 4,122,192 | 10/1978 | Fellows | 424/333 |
| 4,251,387 | 2/1981 | Lim et al. | 424/32 |
| 4,428,983 | 1/1984 | Nehen et al. | 71/64.11 |

Primary Examiner—William R. Dixon, Jr.
Assistant Examiner—C. Johnson
Attorney, Agent, or Firm—Patricia A. Coburn; Richard H. Shear

[57] ABSTRACT

This invention relates to a process for encapsulation, and particularly to the production of small or minute capsules constituted by a skin or thin wall of polymeric material e.g., polyurea, polyamide, polysulfonamide, polyester, polycarbonate, or polyurethane, which involves first providing an organic liquid (continuous phase liquid) containing an oil soluble alkylated polyvinylpyrrolidone emulsifier A discontinuous (aqueous) phase liquid containing a water-soluble material, which is the material to be encapsulated, plus a first shell wall component; is dispersed in the continuous phase liquid to form a water-in-oil emulsion. The second shell wall component is added to the water-in-oil emulsion whereupon the first shell wall component reacts with the second shell wall component to form a solid polymeric shell wall about the material to be encapsulated. The capsules formed may be directly used as in the form of an organic suspension, i.e., a suspension of microcapsules in the organic liquid.

19 Claims, No Drawings

HIGH CONCENTRATION ENCAPSULATION OF WATER SOLUBLE-MATERIALS

BACKGROUND OF THE INVENTION

This invention relates to a process for producing small or minute capsules containing a water-soluble material which comprises dissolving a first shell wall component in the water-soluble material, which is the material to be encapsulated, dispersing the resulting mixture, said mixture being the aqueous or discontinuous phase liquid into an organic or continuous phase liquid containing an emulsifier which is an oil soluble alkylated polyvinylpyrrolidone polymer to form a water-in-oil (W/O) emulsion and thereafter adding a second shell wall component (usually dissolved in additional oil phase liquid) to the water-in-oil emulsion whereby the second shell wall component reacts with the first shell wall component to form a polymeric shell wall about the water-soluble material at the water/oil interface.

The process of microencapsulation described herein is a modification of known interfacial polycondensation techniques. Such techniques are thoroughly described in the literature. An article entitled "Interfacial Polycondensation, a Versatile Method of Polymer Preparation" by P. W. Morgan, Society Plastics Engineers Journal 15, 485–495 (1959), provides a good summary of the reactions involved and the polymers which can be used in this method. The use of the technique of interfacial polymerization in a process of microencapsulation is also known; e.g., MICROCAPSULE PROCESSING AND TECHNOLOGY, Asaji Kondo, Edited by J. Wade Von Valkenburg, pp. 35–45, Marcel Dekker, Inc., New York, NY 10016 (1979). Exemplary of the patents directed to microencapsulation of water-soluble materials via interfacial polycondensation reaction are U.S. Pat. Nos. 3,429,827, 3,577,515, 3,575,882 and 4,251,387.

Microencapsulation of water-soluble materials utilizing an interfacial polycondensation reaction generally involves the following procedure. A first reactive monomeric or polymeric material(s) (first shell wall component) is dissolved in the material to be encapsulated to form the aqueous or discontinuous phase liquid. The discontinuous phase liquid is dispersed into an oily (organic) or continuous phase liquid to form a water-in-oil (W/O) emulsion. The continuous phase (organic) liquid may contain a second reactive monomeric or polymeric material (second shell wall component) at the time the discontinuous phase is dispersed into the continuous phase. If this is the case, the first and second shell wall components will immediately begin to react to form a polycondensate shell wall about the material to be encapsulated. However, the preferred practice is to form the W/O emulsion before the second shell wall component is added to the emulsion. This enhances the formation of a stable W/O emulsion before the interfacial polycondensation reaction is initiated.

The capsules produced in this fashion may be any desired size, for example, of the order of 1 micron up to 100 microns or larger in diameter, preferably the size of the microcapsules will range from about 1 to about 50 microns in diameter. Capsules of this character have a variety of uses, as for containing water-soluble dyes, inks, chemical agents, pharmaceuticals, flavoring materials, water-soluble pesticides, e.g., herbicides, plant growth regulants, insecticides, fungicides, and the like.

Any water-soluble material into which the first shell wall component can be dissolved and which is nonreactive with said first shell wall component may be encapsulated with this process. Once encapsulated, the liquid or other form is preserved until it is released by some means or instrumentality that breaks, crushes, melts, dissolves, or otherwise removes the capsule skin or until release by diffusion is effected under suitable conditions.

A method of encapsulating water-soluble materials by interfacial condensation between directacting, complimentary reactants is disclosed in U.S. Pat. No. 3,577,515, which describes a method which requires a first reactant (shell wall component) and a second reactant (shell wall component) complimentary to the first reactant, with each reactant in separate phases, such that the first and second reactants react to form encapsulated droplets of water-soluble or water-immiscible material. The process is applicable to a variety of polycondensation reactions, i.e., to many different pairs of reactants capable of interfacial condensation from respective carrier liquids to yield solid film at the liquid interface. The resulting capsule skin may be produced as a polyamide, polysulfonamide, polyester, polycarbonate, polyurethane, polyurea or mixtures of reactants in one or both phases so as to yield corresponding condensation copolymers.

Although it is known in the art, e.g., U.S. Pat. No. 3,464,926 and U.S. Pat. No. 3,577,515, that microencapsulation of water-soluble materials is possible using well known emulsifiers, e.g. lecithin or "Span 60", to prepare water-in-oil emulsions, emulsions made with these common emulsifiers do not support shell wall forming reactions at the water/oil interface when there is a high concentration of aqueous phase to be microencapsulated. The process described by U.S. Pat. No. 3,577,515 and U.S. Pat. No. 3,575,882, while adequate if one desires to encapsulate low concentrations of water-soluble materials, is inadequate if concentrated amounts, i.e., greater than 480 grams/liter of aqueous or discontinuous phase liquid is to be encapsulated.

Surprisingly, it has been discovered that through the use of an oil-soluble alkylated polyvinylpyrrolidone (PVP) polymer one is able to form high concentration water-in-oil emulsions which are sufficiently stable to allow chemical reaction at the water/oil interface. The present invention thus provides a new and improved encapsulation process via an interfacial polycondensation reaction which is rapid and effective to encapsulate high concentrations of water-soluble materials.

The critical feature of the present invention resides in the use of the specific emulsifiers described herein to form a sufficiently stable water/oil emulsion so that a concentrated amount of water-soluble material is present in the aqueous or discontinuous phase and is thereafter encapsulated. Generally, there will be greater than 480 grams of aqueous or discontinuous phase liquid per liter of total composition. The finished microcapsules do not agglomerate nor does the capsule mass solidify when stored for extended periods of time or when exposed for short periods to elevated temperatures.

The invention is applicable to a large variety of polycondensation reactions, i.e., to many different pairs of reactants capable of interfacial condensation at the organic/aqueous phase interface to form microcapsules. A number of basic types of polycondensation reactions, are known and can be utilized in the present process. Thus, as examples, the resulting capsule skin or enclosure may be produced as a polyamide, polysulfonamide, polyester, polycarbonate, polyurethane, or polyurea, and the reactions of the invention may also involve mixtures of reactants in one or both phases, so as to yield corresponding condensation copolymers if desired, e.g., mixed polyamide/polyester, or polyamide/polyurea capsule shell walls.

The present invention is particularly advantageous when employed to encapsulate liquid fertilizers, herbicides, e.g., isopropylamine salt of N-phosphonomethylglycine, potassium salt of dicambaa and the tetramethylammonium salt of 2,4-D, plant growth regulators, insecticides, fungicides and the like.

The process of this invention is particularly advantageous if the continous phase, i.e., the organic liquid is itself a pesticide as for example, the herbicides alachlor, metalachlor, 2-chloro-N-(ethoxymethyl)-6'-ethyl-O-acetolindide, etc. Through the use of the process of this invention one is able to produce a composition containing a mixture of two or more incompatible active agents, for example, a water-soluble herbicide like the isopropylamine salt of glyphosate dispersed throughout an oil-soluble herbicide like alachlor. Formulation additives such as film forming agents can be added directly to the final suspension to improve the adhesion of the microcapsules to foliage, the dispersion of the organic phase liquid in water, etc. In some cases, reduced toxicity and extended activity of encapsulated herbicides and pesticides may result.

DETAILED DESCRIPTION OF THE INVENTION

The invention relates to a process of encapsulating a water-soluble material within a shell wall of polymeric material, e.g., polyurea, polyamide, polysulfonamide, polyester, polycarbonate, or polyurethane. The procedure of the invention involves first providing an organic liquid containing an oil-soluble alkylated polyvinylpyrrolidone (PVP) polymer; this organic liquid becomes the continuous phase. An aqueous or discontinuous phase liquid which is the water-soluble material (the material to be encapsulated) with the first shell wall component, dissolved therein is thereafter added to the organic or continuous phase liquid, with agitation, to form a dispersion of small droplets of aqueous or discontinuous phase droplets throughout the organic phase; i.e., a water-in-oil emulsion is formed. Thereafter, a second shell wall component is added, with continued agitation, to the water-in-oil emulsion. The second shell wall component reacts with said first shell wall component to form a shell wall about the water-soluble material.

The water-soluble material referred to herein is the material to be encapsulated and is suitably any water-soluble material into which the first shell wall component can be dissolved and which is nonreactive thereto. As used hereafter, the term "water-soluble material" means an aqueous solution of a water-soluble chemical; that is, the water-soluble material is the aqueous or discontinuous phase liquid. Such materials as water-soluble dyes and inks, pharmaceuticals, herbicides, e.g., isopropylamine salt of N-phosphonomethylglycine, potassium salt of dicamba and the tetramethylammonium salt of 2,4-D, plant growth regulants, e.g., gallic acid, ethanedial dioxine (gloxime), insecticides, e.g., hexamethyl-phosphoric triamide, S-[2-(ethylsulfinize)ethyl]O,O-dimethylphosphorothioate, fungicides, nematocides and the like may be encapsulated by the process of the invention.

In the practice of the preferred embodiment of the present invention, the material to be encapsulated is an agricultural chemical, as, for example, a herbicide, plant growth regulator, insecticide, fungicide, or the like.

In utilizing the process of the present invention, the material to be encapsulated need not consist of only one type, but may be a combination of two or more various types of water-soluble materials. For example, employing an appropriate water-soluble material, such a combination is an active herbicide with another active herbicide or an active herbicide and an active insecticide.

The water-soluble material containing the first shell wall component dissolved therein comprises the aqueous or discontinuous phase liquid. The water-soluble material preferably acts as the solvent for the first shell wall component thus avoiding the use of additional aqueous liquid solvents and allowing for a concentrated amount of water-soluble material in the final encapsulated product. The water-soluble material and first shell wall component are added simultaneously to the organic (continuous) phase liquid in a pre-mixed state. That is, the water-soluble material and first shell wall component are pre-mixed to obtain a homogeneous aqueous or discontinuous phase liquid before addition to and emulsification in the continuous phase liquid to form the water-in-oil emulsion.

The concentration of water-soluble material initially present in the discontinuous phase should be sufficient to provide at least about 480 grams of aqueous or discontinuous phase liquid per liter of total composition. However, this is by no means limiting and a greater amount can be used. In practical operation, as will be recognized by those skilled in the art, the use of extremely high concentrations of water-soluble material will result in very thick suspensions of microcapsules. In general, the concentration of aqueous or discontinuous phase liquid will range from about 480 grams to about 700 grams per liter of total composition. The preferred range is from about 480 grams to about 600 grams per liter of total composition.

As used herein, the term "first shell wall component" refers to a material or mixture of materials which is soluble in the material to be encapsulated and which is capable of reacting with the second shell wall component to form a polymeric shell wall about the material to be encapsulated. The material to be encapsulated together with the first shell wall component constitute the aqueous or discontinuous phase liquid. The term "second shell wall component", as used herein, refers to a water-insoluble material, i.e., a material which is insoluble in the aqueous phase. Further, the second shell wall component must be soluble in the organic or continuous phase liquid and non-reactive thereto. The second shell wall component must react with the first shell wall component to form a polymeric shell wall about the material to be encapsulated.

The following illustrates the type of polymeric shell wall formed when various first and second shell wall components are utilized in the process of encapsulation described herein:

| First Shell Wall Component | Second Shell Wall Component | Polymeric Shell Wall |
|---|---|---|
| Diamine or Polyamine | Diacid or Polyacid Chlorides | Polyamide |

-continued

| First Shell Wall Component | Second Shell Wall Component | Polymeric Shell Wall |
|---|---|---|
| Diamine or Polyamine | Dichloroformates or Polychloroformates | Polyurethane |
| Diols or Polyols | Diisocyanates or Polyisocyanates | Polyurethane |
| Diamine or Polyamine | Disulfonyl or Polysulfonyl Chlorides | Polysulfonamide |
| Diamine or Polyamine | Diisocyanates or Polyisocyanate | Polyurea |
| Diols or Polyols | Diacid or Polyacid Chlorides | Polyester |
| Diols or Polyols | Dichloroformates or Polychloroformates | Polycarbonate |

As more specific instances of polycondensation reactions to which the present encapsulation process is applicable, the following may be mentioned: diamines or polyamines in the aqueous liquid (discontinuous) phase and diacid or polyacid chlorides in the organic (continuous) phase liquid yield capsule walls consisting of polyamides. Diamines or polyamines in the aqueous liquid and dichloroformates or polychloroformates in the organic liquid yield a polyurethane capsule skin. Diamines or polyamines in the aqueous liquid and disulfonyl or polysulfonyl chlorides in the organic liquid produce a polysulfonamide capsule skin. Diamines or polyamines in the aqueous phase liquid and a diisocyanate or polyisocyanate in the organic phase liquid produce a polyurea skin. With diols or polyols in the aqueous liquid and diacid or polyacid chlorides in the organic phase liquid, polyester shell walls are produced. When dichloroformates or polychloroformates are used in the organic liquid and diols or polyols in the aqueous liquid, the capsule skins are polycarbonates.

It will further be appreciated that not only are there other complementary intermediates which react to form polycondensates in a direct manner useful in the interfacial condensation process of encapsulation, but various mixtures of intermediates, i.e., mixtures of shell wall components may be employed in either or both of the aqueous and organic phases. For example, mixtures of diols and diamines in the aqueous liquid and an acid chloride(s) in the organic liquid are useful to achieve polyester/polyamide condensation copolymers. Also, diamines or polyamines in the aqueous liquid and mixtures of diacid or polyacid chlorides and diisocyanates or polyisocyanates in the organic liquid produce a polyamide/polyurea skin.

Examples of suitable difunctional acid-derived shell wall components suitable for use in the continuous (organic) phase liquid are sebacoyl chloride, ethylene bischloroformate, phosgene, terephthaloyl chloride, adipoyl chloride, azelaoyl chloride (azelaic acid chloride), dodecanedioic acid chloride, dimer acid chloride, and 1,3-benzenesulfonyl dichloride. Polyfunctional compounds of this type are exemplified by trimesoyl chloride, 1,2,4,5 benzene tetracid chloride, 1,3,5 benzene trisulfonyl chloride, trimer acid chloride, citric acid chloride, and 1,3,5 benzene trischloroformate. Intermediates similarly useful in the continuous or organic phase also include diisocyanates, hexamethylene diisocyanate and polymethylene polypheylisocyanate.

Examples of suitable diols for use as intermediates in the aqueous phase are bisphenol A [2,2 bis-(p,p'-dihydroxy diphenyl)propane], hydroquinone, resorcinol, catechol, and various glycols such as ethylene glycol, pentanediol, hexanediol, dodecanediol, 1,4-butanediol and the like. Polyfunctional alcohols of this character, e.g., triols, are exemplified by pyrogallol (1,2,3-benzenetriol), phloroglucinol dihydrate, pentaerythritol, trimethylolpropane, 1,4,9,10-tetrahydroxyanthracene, 3,4-dihydroxyanthranol, diresorcinol and tetrahydroxyquinone.

Instances of suitable diamines and polyamines, usually selected as water soluble per se or in water soluble salt form, where such reactant is to be included in an aqueous phase, are ethylene diamine, phenylene diamine, toluene diamine, hexamethylene diamine, diethylene triamine and piperazine. Amines which are effective as polyfunctional reactants, are, e.g., 1,3,5-benzene triamine trihydrochloride, 2,4,6-triamino toluene trihydrochloride, polyethylene imine, 1,3,6 triaminonaphthalene, 3,4,5 triamino-1,2,4 triazole, melamine, and 1,4,5,8 tetramino anthraquinone. Amines which have a functionality greater than 2 but less than 3 and which may provide a degree of crosslinking in the shell wall are the polyalkylene polyamines of the type, e.g., tetraethylene pentamine, pentaethylene hexamine, and the like.

The first shell wall component and the second shell wall component form the shell wall which encapsulates the water-soluble material. The shell wall content of the capsules formed by the present process may vary from about 5 percent to about 30 percent, preferably 8 to 20 percent and more particularly, 10 percent by weight, of the water-soluble material.

The amount of first shell wall component and second shell wall component used in the process is determined by the percent shell wall content produced. Generally, there will be present in the reaction from about 1.5% to about 10.0% first shell wall component relative to the weight of the water-soluble material, preferably from about 2.0% to about 5.0% by weight of said water-soluble material. There will be from about 3.5% to about 20.0% second shell wall component, relative to the weight of the water-soluble material, present in the reaction, preferably from about 3.5% to about 10.0% by weight of said water-soluble material. Although a stoichiometric amount of second shell wall component has been used herein, it should be recognized that excess second shell wall component may be used without departing from the spirit or scope of the present invention.

The organic or continuous phase liquid referred to herein is suitably any liquid, oil, meltable solid or solvent soluble material, into which the second shell wall component can be dissolved and which is nonreactive thereto. Such materials as organic solvents such as xylene, monochlorobenzene, methylene chloride, etc., oily herbicides or meltable solid herbicides, e.g., 2-chloro-2',6'-diethyl-N-methoxymethyl acetanilide (commonly known as alachlor), N-butoxymethyl-α-chloro-2',6'-diethylacetanilide (commonly known as butachlor), 2'-methyl-6'-ethyl-N-(1-methoxyprop-2-yl)-2-chloroacetanilide (commonly known as metolachlor), 2'-t-Butyl-2-chloro-N-methoxymethyl-6'-methylacetanilide, α-Chloro-N-(2-methoxy-6-methylphenyl)-N-(1-methylethoxymethyl)acetamide, α-Chloro-N-(ethoxymethyl)-N-[2-methyl-6-(trifluoromethyl)phenyl]-acetamide, α-Chloro-N-methyl-N-[2-methyl-6-(3-methylbutoxy)phenyl]acetamide, α-Chloro-N-methyl-N-(2-methyl-6-propoxyphenyl)acetamide, N-(2-butoxy-6-methylphenyl)-α-chloro-N-methyl acetamide, Isobutyl ester of (2,4-dichlorophenoxy)a- cetic acid, 2-Chloro-N-(ethoxymethyl)-6′-ethyl-o-acetatoluidide, 1-(1-cyclohexen-1-yl)-3-(2-fluorophenyl)-1-methyl urea, S-2,3,3-trichloroallyl-diisopropyl thiocarbamate (commonly known as triallate), S-2,3-dichloroallyldiisopropylthiocarbamate (commonly known as diallate), α,α,α-trifluoro-2,6-dinitro-N,N-dipropyl-p-toluidine (commonly known as trifluralin), insecticides, e.g., methyl and ethyl parathion, and herbicidal safeners (antidotes), e.g., 5-thiazolecarboxylic acid, 2-chloro-4-(trifluoromethyl)-, (phenylmethyl)ester, are specifically contemplated herein.

In the practice of the preferred embodiment of the present invention, the continuous phase liquid is an agricultural chemical, as, for example, a herbicide, plant growth regulator, insecticide, or the like.

The emulsifying agent, which is critical for use in the practice of the present invention to produce high concentration microencapsulation of concentrated amounts of water-soluble materials, is an oil-soluble alkylated polyvinylpyrrolidone (PVP) polymer.

Exemplary of such materials is "GAF V-216" and "GAF V-220" available from GAF Corporation, Chemical Products, 140 W. 51st St., New York, NY 10020. "GAF V-216" is a PVP alkylated with $C_{16}$ alkyl groups, "GAF V-220" is a PVP alkylated with $C_{20}$ alkyl groups.

The range of emulsifier concentration found most acceptable in the system will vary from about 0.5 percent to about 15 percent and preferably from about 2 percent to about 6 percent, based on the weight of the water-soluble material and most preferably at from about 2.0 to about 4.0 percent and most preferably 2.0 percent relative to the weight of the water-soluble material.

The microcapsules of the present invention require no additional treatment such as separation from the organic liquid, but may be directly utilized or combined with, e.g., oil-soluble herbicides, insecticides, or the like to form organic suspensions, i.e., a suspension of microcapsules in an organic liquid which may be conveniently applied in agricultural uses. Most often it is most convenient to bottle or can the organic suspension containing the encapsulated water-soluble material, in which case it may be desirable to add formulation ingredients to the final organic suspension of microcapsules. Formulation ingredients such as density balancing agents, thickeners, biocides, surfactants, dispersants, anti-freeze agents, and the like can be added to improve stability and ease of application.

The process of the present invention is capable of satisfactory performance and production of encapsulated material without adjustment to specific pH value. In general, no adjustment of the pH of the system need be made during the encapsulation process. In the event such adjustment is necessary, choice of an appropriate acid or base is within the skill of the art.

In the practice of the invention, the temperature of the process may for the most part be room temperature; however, in the event the organic phase liquid is a meltable solid, e.g., alachlor, the temperature of the process should be maintained above the melting point of the organic material but below the temperature wherein the polymeric shell wall would begin to hydrolyze or otherwise break down. For example, where it is desired to use alachlor herbicide as the continuous phase liquid, it will be necessary to heat the alachlor herbicide to its molten state. Alachlor herbicide melts at 39.5° C. to 41.5° C. and the temperature of the process should accordingly be maintained above about 41.5° C.

The agitation employed to establish the dispersion of water-soluble phase droplets in the aqueous phase may be supplied by any means capable of providing suitably high shear, that is, any variable shear mixing apparatus, e.g., a blender, a Brinkman Polytron homogenizer, Ross Model 100L homogenizer, and the like, can be usefully employed to provide the desired agitation.

The particular size of the microcapsules will range from about 1 micron up to about 100 microns in diameter. From about 1 to about 10 microns is an optimum range. From about 5 to about 50 microns is satisfactory for formulating.

The present invention will be further explained by reference to the following examples which are merely illustrative and not limiting in nature. Unless otherwise indicated, the examples which follow were prepared as follows: the water-soluble material, containing the first shell wall component(s) dissolved therein was emulsified into the organic or continuous phase liquid containing the emulsifier; the emulsion was formed with the aid of shear. The second shell wall component(s), usually dissolved in an additional amount of organic phase liquid, was thereafter added to the emulsion and after a short period of time, the shear rate was reduced and shear was continued for varying periods of time.

EXAMPLE 1

Water In Crop Oil, Polyurea Shell Wall

| Ingredient | Grams | |
|---|---|---|
| Water | 200.00 | |
| 2,4,6-Triaminopyramidine | 4.86 | Aqueous |
| 1,6-Hexamethylenediamine | 4.86 | Phase |
| GAF V-216, Alkylated PVP | 10.00 | Oil |
| Crop Oil 7N, Paraffinic Oil | 150.00 | Phase |
| 1,6-Hexamethylenediisocyanate | 10.32 | Oil Soluble |
| Crop Oil 7N, Paraffinic Oil | 20.00 | Monomer Solution |

The emulsion formed well. Uniform, individual 1–10 micron diameter sperical microcapsules were seen upon microscopic examination. After several months the heavier microcapsules settled to the base of the lighter oil phase; however these were readily redispersed with gentle shaking of the bottle. There was no separation of aqueous phase from oil phase.

EXAMPLE 2

Liquid Nitrogen Fertilizer In Crop Oil, Polyester Shell Walls

| Ingredient | Grams | |
|---|---|---|
| 28%-N, Liquid Fertilizer | 200.00 | |
| 1,5-Pentanediol | 6.46 | Aqueous |
| 1,3,5-Benzenetriol | 0.71 | Phase |
| NaOH, 50% | 11.23 | |
| GAF V-216, Alkylated PVP | 3.93 | Oil |
| Crop Oil 7N | 130.00 | Phase |
| Adipyl Chloride | 12.84 | Oil Soluble |
| Crop Oil 7N | 4.70 | Monomer Solution |

The emulsion formed well and was somewhat thick. After addition of the adipyl chloride, the emulsion thinned and became clear in appearance. Individual, uniform 1–10 micron diameter microcapsules were observed microscopically. After several months, the microcapsules settled to the base of the bottle with clear crop oil above. The sedimented microcapsules readily redispersed with gentle shaking of the bottles. There was no separation of the aqueous liquid from oil phase liquid.

EXAMPLE 3

Water Soluble Herbicide In Polyurethane Shell Wall

| Ingredient | Grams | |
|---|---|---|
| Isopropylamine Salt of | | |
| N—phosphonomethylglycine (62%) | 200.00 | Aqueous |
| 1,3,5-Benzenetriol | 1.00 | Phase |
| 1,5-Pentanediol | 6.56 | |
| GAF V-216 | 4.23 | Oil |
| Crop Oil 7N | 130.00 | Phase |
| 1,6-Hexamethylenediisocyanate | 12.44 | Oil Soluble |
| Crop Oil 7N | 6.30 | Monomer Solution |

The blender jar was wrapped with insulation and heating tape. After hexamethylenediisocyanate was added to the well formed emulsion, the temperature was raised to 70° C. for two hours to complete reaction of the isocyanate and polyol. Microscopically uniform individual spherical microcapsules were observed 1-5 microns in diameter. After several months there was no separation of oil phase from aqueous phase. Settled microcapsules were readily dispersed by shaking the bottle.

EXAMPLE 4

Water in Polyester Shell Wall

| Ingredient | Grams | |
|---|---|---|
| Water | 200.00 | |
| 1,5-Pentanediol | 6.46 | Aqueous |
| 1,3,5-Benzenetriol | 0.71 | Phase |
| NaOH, 50% | 11.23 | |
| Monochlorobenzene | 200.00 | Oil |
| GAF V-216 Alkylated PVP | 4.00 | Phase |
| Adipyl Chloride | 12.84 | Oil Soluble |
| Monochlorobenzene | 21.00 | Monomer Solution |

The emulsion formed well. There was no change after addition of adipyl chloride. MIcroscopically, spherical, individual microcapsules 1-10 microns in diameter were observed. After several months, settled microcapsules were readily redispersed when the bottle was shaken. The MCB was a clear liquid at the base of the bottle; there was no separation of oil phase from liquid phase.

EXAMPLE 5

Liquid Fertilizer in Xylene, Polyamide Shell Wall

| Ingredient | Grams | |
|---|---|---|
| Liquid Fertilizer, 28% Nitrogen | 200.00 | |
| 1,6-Hexamethylenediamine, 50% | 7.07 | Aqueous |
| 2,2',2"-Triamino triethylamine | 4.10 | Phase |
| NaOH, 50% | 11.30 | |
| GAF V-216, Alkylated PVP | 4.00 | Oil |
| Xylene | 125.00 | Phase |
| Adipyl Chloride | 12.93 | Oil Soluble |
| Xylene | 12.80 | Monomer Solution |

Microscopically, spherical individual microcapsules, 1-5 microns in diameter, were formed. After several months, settled microcapsules were readily resuspended. There was no separation of liquid phase from phase oil.

EXAMPLE 6

Water in Methylnaphthalene, Polyurethane Shell Wall

| Ingredient | Grams | |
|---|---|---|
| Water | 180.00 | Aqueous |
| 1,5-Pentanediol | 5.04 | Phase |
| GAF V-216, Alkylated PVP | 4.00 | Oil |
| Methylnaphthalene | 130.00 | Phase |
| Polymethylene polyphenyl | | Oil Soluble |
| isocyanate | 12.96 | Monomer |
| Methylnaphthalene | 6.85 | Solution |

The blender jar was wrapped in insulation and heating tape. After the isocyanate was added to the emulsion the temperature was raised to 70° C. for two hours to complete reaction of the isocyanate and diol. The emulsion formed well. There was no change following addition of the isocyanate. Microscopically, uniform, spherical, individual microcapsules 1-2 microns in diameter were formed. After several months, lightly settled microcapsules were readily resuspended. There was no separation of aqueous phase from oil phase.

EXAMPLE 7

Potassium Salt Solution of Dicamba in Crop Oil, Polyurethane Shell Wall

| Ingredient | Grams | |
|---|---|---|
| Potassium-Dicamba, 37.7% | 50.00 | Aqueous |
| 1,5-Pentanediol/1,3,5- | | Phase |
| Benzenetriol (5:1) | 1.89 | |
| GAF V-216 | 0.50 | Oil |
| Crop Oil | 49.50 | Phase |
| 1,6-Hexamethylenediisocyanate | 3.11 | Oil Soluble |
| Crop Oil | 10:50 | Monomer Solution |

The blender jar was wrapped with insulation and heating tape. After hexamethylenediisocyanate was added to the emulsion, the temperature was raised to 70° C. for two hours to complete reaction of the isocyanate and polyol. Microscopically, 1-20 micron diamter spherical, individual microcapsules were observed. After several months, settled microcapsules were easily redispersed by shaking the bottle. There was no separation of aqueous phase from oil phase.

EXAMPLE 8

Tetramethylammonium 2,4-D Solution in Crop Oil, Polyurethane Shell Wall

| Ingredient | Grams | |
|---|---|---|
| Tetramethylammonium 2,4-D, 50% | 50.00 | Aqueous |
| 1,5-Pentanediol/1,3,5- | | Phase |
| Benzentriol (3:1) | 1.89 | |
| GAF V-216 | 1.50 | Oil |
| Crop Oil | 40.00 | Phase |
| 1,6-Hexamethylenediisocyanate | 3.11 | Oil Soluble |
| Crop Oil | 3.50 | Monomer Solution |

The blender jar was wrapped with insulation and heating tape. After hexamethylenediisocyanate was added to the emulsion, the temperature was raised to 70° C. for two hours to complete reaction of the isocyanate and polyol. Microencapsules were 1-20 microns in size. There was no separation of oil phase from aqueous phase with time.

EXAMPLE 9

Potassium Salt of Dicamba in Crop Oil, Polyester Shell Wall

| Ingredient | Grams | |
|---|---|---|
| Potassium dicamba solution (35.3%) | 50.00 | Aqueous |
| KOH | 1.90 | Phase |
| 1,5-Pentanediol/1,3,5-Benzentriol (3:1) | 1.82 | |
| GAF V-216 | 1.00 | Oil |
| Crop Oil | 42.40 | Phase |
| Adipyl Chloride | 3.18 | Oil Soluble |
| Crop Oil | 10.00 | Monomer Solution |

The emulsion was somewhat thick. After adding adipyl chloride the emulsion thinned and became opaque white. Microcapsules, 1-5 microns in diameter, were observed. There was no separation of oil phase from liquid phase with time. Settled microcapsules were readily resuspended when the bottle was shaken.

EXAMPLE 10

Isopropylamine Salt of N-Phosphonomethylglycine (IPA Salt) In Alachlor, Polyurethane Shell Wall This is an example of a meltable solid herbicide being used as the continuous phase into which a water soluble herbicide is microcapsulated. After microencapsulation was completed, the suspension was formulated to keep the continuous phase herbicide liquid at use temperatures. All equipment and ingredients were at 50° C. during preparation of the organic suspension. Composition is as follows:

| Ingredient | Grams | |
|---|---|---|
| IPA Salt (62%) | 217.70 | Aqueous |
| 1,5-Pentanediol | 7.14 | Phase |
| 1,3,5-Benzentriol | 1.10 | |
| GAF, V-216 | 4.50 | Oil |
| Alachlor, 95% | 185.00 | Phase |
| 1,6-Hexamethylenediisocyanate | 13.54 | Oil Soluble |
| Alachlor, 95% | 25.00 | Monomer Solution |
| *Stepan Agent 884-56 | 50.00 | Formulation |
| Monochloro benzene | 280.00 | Ingredients |

*Stepan Agent 884-56 is a proprietary anionic/nonionic emulsifier blend which is manufactured by Stepan Chemicals Edens & Winnetka Roads, Northfield, IL 60093.

The blender jar was wrapped with insulation and heating tape. After hexamethylenediisocyanate was added to the emulsion, the temperature was raised to 70° C. for two hours to complete reaction of the isocyanate and polyol. Microscopically, individual, spherical microcapsules 1-5 microns in diameter were observed. There was no separation of oil phase and aqueous phase.

In addition to the previously described advantages of the present invention, microencapsuation of water-soluble agricultural chemicals like herbicides, insecticides, fungicides, plant growth regulants, and the like may, in general, offer several advantages over conventional formulations. Thus, for example, microencapsulation of a broad leaf herbicide (e.g. dicamba) using an acetamide herbicide (e.g. alachlor) as the continuous phase liquid may stabilize the water-soluble broad leaf herbicide against washing out of the root zone, which would allow for preemergence application of the broadleaf herbicide without concern for early season rains. Microencapsulated herbicide formulations may, in some cases, be less phytotoxic to certain crop plants, thereby enhancing the crop safety of the herbicide and may also protect the herbicides from environmental degradation, reduce leaching of the herbicide into the soil, and thus prolong or increase the soil life of the herbicide. It can be appreciated that microencapsulated agricultural chemical formulations have several advantages which make such microencapsulated formulations a desirable and beneficial alternative to conventional agricultural chemical formulations.

A particular object of the present invention is to provide an agricultural chemical composition consisting essentially of a suspension in an organic liquid of microcapsules comprised of a water-soluble agricultural chemical, especially a herbicide contained within an encapsulating wall of condensation polymer where the organic liquid is itself an agricultural chemical, e.g. a herbicide. The concentration of agricultural chemical present in such compositions will be about 480 grams per liter of aqueous suspension or greater, preferably from about 480 grams to about 700 grams per liter of aqueous suspension and more preferably, from about 480 grams to about 600 grams per liter of total composition.

It is to be understood that the present invention is not limited to the specific embodiments shown and described herein, but may be carried out in other ways without departure from its spirit or scope.

What is claimed is:

1. A process of encapsulating a water-soluble material within a shell wall of polymeric materials which comprises:
   (a) providing an organic continuous phase liquid containing an oil soluble alkylated polyvinylpyrrolidone emulsifier;
   (b) dispersing in said continuous phase liquid an aqueous discontinuous phase liquid containing a first shell wall component and a water-soluble material dissolved therein to form a dispersion of discontinuous phase droplets throughout the continuous phase;
   (c) adding with agitation to said dispersion a second shell wall component, whereby said second shell wall component reacts with said first shell wall component to form a polymeric shell wall about said discontinuous phase droplet;
   wherein the concentration of said water-soluble material is from about 480 grams to about 700 grams per liter of composition; wherein the concentration of said emulsifier is from 0.5% to about 15.0% by weight of said water-soluble material; wherein the concentration of said first shell wall component is from about 1.5% to about 10.0% by weight of said water soluble material and wherein the concentration of said second shell wall component is from about 3.5% to about 20.0% by weight of said water-soluble material.

2. A process according to claim 1 wherein said polymeric shell wall is selected from the group consisting of polyamide, polyurethane, polysulfonamide, polyurea, polyester and polycarbonate or mixtures thereof.

3. A process according to claim 1 wherein said polymeric shell wall is polyurea.

4. A process according to claim 1 wherein said first shell wall component is a difunctional or polyfunctional reactant which is soluble in said water-soluble material and which is capable of reacting with said second shell wall component to form a polymeric shell wall about said water-soluble material.

5. A process according to claim 1 wherein said second shell wall component is a water-insoluble material which is capable of reacting with said first shell wall component to form a polymeric shell wall about said water-soluble material.

6. A process according to claim 3 wherein said second shell wall component is a polyisocyanate and wherein said first shell wall component is a difunctional or polyfunctional amine.

7. A process according to claim 3 wherein said second shell wall component is a diisocyanate and said first shell wall component is a polyfunctional amine or a mixture of polyfunctional and difunctional amines.

8. A process according to claim 1 wherein the concentration of said water-soluble materal is from about 480 grams to about 600 grams per liter of composition and wherein the concentration of emulsifier is from about 2.0% to about 4.0% by weight of said water-soluble material.

9. A process according to claim 8 wherein said water-soluble material is isopropylamine salt of N-phosphonomethylglycine and said continuous phase liquid is 2-chloro-2',6'-diethyl-N-methoxymethyl acetanilide or 2'-methyl-6'-ethyl-N-(1-methoxy-prop-2-yl)-2-chloroacetanilide or 2-chloro-N-(ethoxymethyl)-6'-ethyl-o-acetatoluidide.

10. A process according to claim 1 wherein the average particle size of the microcapsules produced by said process is in the range of from about 1 micron to about 50 microns in diameter.

11. A composition consisting essentially of microcapsules suspended in an organic liquid comprising a water-soluble material contained within an encapsulating wall of polymeric material wherein:
   (a) the concentration of said water-soluble material is from about 480 grams to about 700 grams per liter of composition;
   (b) wherein said encapsulating wall of polymeric material is the reaction product of a first shell wall component which is a difunctional or polyfunctional reactant that is soluble in said water-soluble material and a second shell wall component which is water insoluble and which is a difunctional or polyfunctional reactant and wherein concentration of first shell wall component is from about 1.5% to about 10.0% relative to the weight of said water-soluble material and wherein the concentration of said second shell wall component is from about 3.5% to about 20.0% relative to the weight of said water-soluble material; and
   (c) wherein said organic liquid contains from about 0.5% to about 15% by weight of said water-soluble material of an oil soluble alkylated polyvinylpyrrolidone emulsifier.

12. A composition as described in claim 11 wherein said polymeric shell wall is polyurea.

13. A composition as described in claim 11 wherein the concentration of said water-soluble material is from about 480 grams to about 600 grams per liter of composition, wherein the concentration of said first shell wall component is from about 2.0% to about 5.0% relative to the weight of said water-soluble material, wherein the concentration of said second shell wall component is from about 5.0% to about 10.0% relative to the weight of said water-soluble material, and wherein the concentration of said emulsifier is from about 2.0% to about 6.0% relative to the weight of said water-soluble material.

14. A composition as described in claim 13 wherein the concentration of said first shell wall component is about 4.0% relative to the weight of said water-soluble material, wherein the concentration of said second shell wall component is about 6.5% relative to the weight of said water-soluble material and wherein the concentration of said emulsifier is about 2% relative to the weight of said water-soluble material.

15. A composition as described in claim 11 wherein said water-soluble material is an herbicide, insecticide, plant growth regulant or an herbicidal antidote.

16. A composition as described in claim 15 wherein said organic liquid is alachlor, butachlor, metolachlor, triallate or diallate herbicides.

17. A composition according to claim 11 wherein the organic liquid additionally contains from 1% to 10% of formulation ingredients based on the weight of the total composition.

18. A composition consisting essentially of a mixture of organic liquid and microcapsules containing a water-soluble material, said mixture being produced by a process which comprises the steps of:
   (a) providing an organic (continuous) phase liquid containing an oil soluble alkylated polyvinylpyrrolidone emulsifier;
   (b) dispersing in said continuous phase, an aqueous (discontinuous) phase consisting essentially of a first shell wall component dissolved in said water-soluble material, to form a dispersion of discontinuous droplets throughout the continuous phase;
   (c) adding, with agitation, to said dispersion a second shell wall component whereby said second shell wall component reacts with said first shell wall component to form a polymeric shell wall about said water-soluble material;
   (d) wherein the concentration of said water-soluble material is from about 480 grams to about 700 grams per liter of said composition, wherein the concentration of first shell wall component is from about 1.5% to about 10.0% by weight of said water-soluble material, wherein the concentration of said second shell wall component is from about 3.5% to about 20.0% by weight of said water-soluble material, and wherein the concentration of said emulsifier is from about 0.5% to about 15% by weight of said water-soluble material.

19. A composition as described in claim 18 wherein said water-soluble material is the isopropylamine salt of N-phosphonomethylglycine, wherein said continuous phase liquid is 2-chloro-2',6'-diethyl-N-methoxymethyl acetanilide and wherein said polymeric shell wall is polyurea.

* * * * *